(12) United States Patent
Lee et al.

(10) Patent No.: US 12,427,251 B2
(45) Date of Patent: *Sep. 30, 2025

(54) USER PARAMETER DEPENDENT COST FUNCTION FOR PERSONALIZED REDUCTION OF HYPOGLYCEMIA AND/OR HYPERGLYCEMIA IN A CLOSED LOOP ARTIFICIAL PANCREAS SYSTEM

(71) Applicant: INSULET CORPORATION, Acton, MA (US)

(72) Inventors: Joon Bok Lee, Acton, MA (US); Yibin Zheng, Hartland, WI (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 429 days.

This patent is subject to a terminal disclaimer.

(21) Appl. No.: 17/818,504

(22) Filed: Aug. 9, 2022

(65) Prior Publication Data

US 2022/0379028 A1 Dec. 1, 2022

Related U.S. Application Data

(63) Continuation of application No. 16/789,051, filed on Feb. 12, 2020, now Pat. No. 11,547,800.

(51) Int. Cl.
*A61M 5/172* (2006.01)
*A61K 38/28* (2006.01)
(Continued)

(52) U.S. Cl.
CPC .......... *A61M 5/1723* (2013.01); *A61K 38/28* (2013.01); *A61M 31/002* (2013.01); *G16H 40/63* (2018.01);
(Continued)

(58) Field of Classification Search
None
See application file for complete search history.

(56) References Cited

U.S. PATENT DOCUMENTS 10,987,468 B2 4/2021 Mazlish et al.
11,547,800 B2 * 1/2023 Lee ..................... A61M 31/002
(Continued)

FOREIGN PATENT DOCUMENTS

JP 2016-536039 A 11/2016
WO WO-2018204568 A1 * 11/2018 ......... A61B 5/14503

OTHER PUBLICATIONS

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

*Primary Examiner* — Manuel A Mendez
(74) *Attorney, Agent, or Firm* — Goodwin Procter LLP

(57) ABSTRACT

Exemplary embodiments described herein relate to a closed loop artificial pancreas system. The artificial pancreas system seeks to automatically and continuously control the blood glucose level of a user by emulating the endocrine functionality of a healthy pancreas. The artificial pancreas system uses a closed loop control system with a cost function. The penalty function helps to bound the infusion rate of insulin to attempt to avoid hypoglycemia and hyperglycemia. However, unlike conventional systems that use a generic or baseline parameter for a user's insulin needs in a cost function, the exemplary embodiments may use a customized parameter in the cost function that reflects the individualized insulin needs of the user. The use of the customized parameter causes the cost function to result in insulin dosages over time better suited to the individualized insulin needs of the user. This helps to better avoid hypoglycemia and hyperglycemia.

20 Claims, 10 Drawing Sheets

(51) Int. Cl.
  *A61M 31/00* (2006.01)
  *G16H 40/63* (2018.01)
  *A61M 5/142* (2006.01)

(52) U.S. Cl.
  CPC ............ *A61M 2005/14208* (2013.01); *A61M 2005/1726* (2013.01); *A61M 2205/52* (2013.01); *A61M 2230/201* (2013.01)

(56) References Cited

U.S. PATENT DOCUMENTS

| | | | |
|---|---|---|---|
| 11,878,145 B2* | 1/2024 | Haidar | ................. A61B 5/7275 |
| 2014/0276554 A1* | 9/2014 | Finan | ................ A61M 5/14244 |
| | | | 604/504 |
| 2015/0120317 A1 | 4/2015 | Mayou et al. | |
| 2016/0038673 A1 | 2/2016 | Morales | |
| 2020/0197605 A1* | 6/2020 | Haidar | ................... G16H 50/50 |

* cited by examiner

USER PARAMETER DEPENDENT COST FUNCTION FOR PERSONALIZED REDUCTION OF HYPOGLYCEMIA AND/OR HYPERGLYCEMIA IN A CLOSED LOOP ARTIFICIAL PANCREAS SYSTEM

RELATED APPLICATIONS

This application is a continuation of U.S. patent application Ser. No. 16/789,051, filed Feb. 12, 2020, the contents of which are incorporated herein by reference in their entirety.

BACKGROUND

Patients with type 1 diabetes may be treated with insulin deliveries in different ways. One approach is to manually deliver a correction bolus of insulin to patients as needed. For instance, if a patient's blood glucose level is 170 mg/dL and the target blood glucose level is 120 mg/dL, a bolus of 1 U may be manually delivered to the patient (assuming a correction factor of 1:50). There are some potential problems with manually delivering such boluses to the patient. The patients may deliver improper amounts of insulin in the bolus. For instance, the user may need a significantly lower amount of insulin than the bolus amount of 1 U. The insulin that has been delivered cannot be taken back from the patient's bloodstream. As a result, the delivery of the bolus may put the patient at risk of hypoglycemia.

Another approach is for the insulin to be delivered automatically by an insulin pump system. Some of the insulin pump systems may use a closed loop control system for regulating the amount of insulin delivered at fixed intervals, such as every 5 minutes. The closed loop algorithms used by the control system may employ a penalty for large insulin deliveries that is balanced in a cost function with a penalty for glucose level excursions. The use of the cost function typically results in smaller insulin deliveries that are delivered more frequently than the manually delivered boluses. The closed loop system may reassess a patient's need more often than a manual approach.

SUMMARY

In accordance with an exemplary embodiment, a device controls insulin deliveries to a user from an artificial pancreas. The device includes a monitor interface for interfacing with a glucose monitor to obtain glucose readings for the user from the glucose monitor. The device may include an artificial pancreas interface for communicating with the artificial pancreas to control delivery of insulin to the user. The device may additionally include a processor that is configured to implement a control loop to control the delivery of insulin by the artificial pancreas. The processor may select an insulin delivery dosage for a next delivery among delivery dosage options that has a best cost function value. The cost function may have a glucose cost component reflective of a difference between a glucose level that the dosage option is predicted to produce for the user and a target glucose level for the user. The cost function may have an insulin cost component reflective of how the dosage option differs from a current baseline insulin dosage. Further, the cost function may have a glucose cost weight coefficient for weighting the glucose cost component and an insulin cost weight coefficient for weighting the insulin cost component. At least one of the glucose cost weight coefficient and the insulin cost weight coefficient may have values customized for the user.

In accordance with an exemplary embodiment, a method is performed by a processor. Per the method, a glucose reading for a user is received from a glucose monitor. A dosage for a next delivery of insulin to the user from an artificial pancreas is determined. The determining comprises applying a cost function to a plurality of possible dosages of insulin to the user and selecting a one of the possible dosages of insulin that has a best cost under the cost function. The cost function has a glucose cost component reflective of a difference between a glucose level that the dosage option is predicted to produce for the user and a target glucose level for the user, and an insulin cost component reflective of how the dosage option differs from a current baseline insulin dosage. The cost function has a glucose cost weight coefficient for weighting the glucose cost component and an insulin cost weight coefficient for weighting the insulin cost component. The glucose cost weight coefficient and the insulin cost weight coefficient have values customized for the user. The artificial pancreas is directed to deliver the selected dosage to the user.

A non-transitory computer-readable storage medium may store computer-readable instructions that cause a processor to perform the method.

The processor may direct the artificial pancreas via the artificial pancreas interface to deliver the selected insulin delivery dosage. Only one of the glucose cost weight coefficient and the insulin cost weight coefficient has a value customized for the user in some instances. In other instances, both of the glucose cost weight coefficient and the insulin cost weight coefficient have values customized for the user.

The glucose cost weight coefficient may have a value of a baseline glucose cost weight coefficient multiplied by a value indicative of a ratio of a custom value representative of insulin needs of the user to a baseline value representative of insulin needs. The value indicative of the ratio may be an exponential value of the ratio. The glucose cost weight coefficient may have a value of a baseline glucose cost weight coefficient multiplied by a value indicative of a ratio of a baseline value representative of insulin needs to a custom value representative of insulin needs of the user.

The insulin weight coefficient may have a value of a baseline insulin cost weight coefficient multiplied by a value indicative ratio of a custom value representative of insulin needs of the user to a baseline value representative of insulin needs. The insulin cost weight coefficient may a value of a baseline insulin cost weight coefficient multiplied by a value indicative of a ratio of a baseline value representative of insulin needs to a custom value representative of insulin needs of the user.

The artificial pancreas interface may be a wireless communication interface. The device may be one of a mobile computing device, a smart phone or an insulin pump assembly. The processor may enforce bounds on a parameter used in determining at least one of the glucose cost weight coefficient or the insulin cost weight coefficient that is customized for the user. The processor may be configured to determine at least one of the glucose cost weight coefficient or the insulin cost weight coefficient based on at least one of a correction factor for insulin sensitivity for the user, an insulin to carbohydrate ratio for the user or a basal insulin level for the user. At least one of the glucose cost weight coefficient and the insulin cost weight coefficient may have values customized for the Total Daily Insulin (TDI) user.

DETAILED DESCRIPTION

Figure 1A:
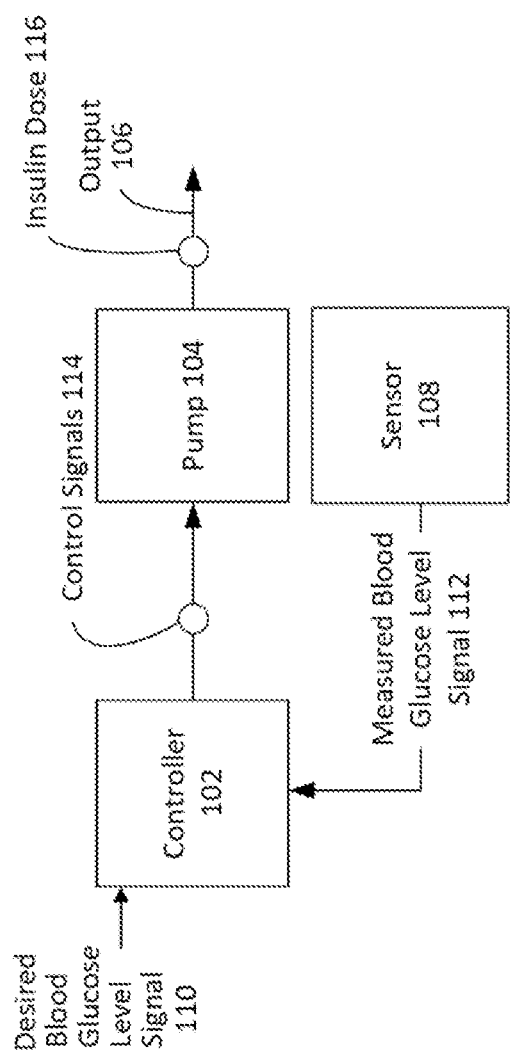
FIG. 1A depicts a simplified block diagram of an illustrative artificial pancreas system.

One difficulty with conventional closed loop approaches for delivering insulin is that the approaches may assess the penalties for all users (e.g., patients) without accounting for differences in the daily insulin needs of patients. The results of this conventional approach may be problematic for users that differ in their daily insulin needs from the norm, such as users that have high insulin needs or low insulin needs. The exemplary embodiments attempt to resolve this issue by using a clinical parameter that captures the user's daily insulin needs to customize the cost function to those daily insulin needs. In particular, the ratio at which the one or more penalties are applied may be modified. For high daily insulin needs, the ratios may be biased towards penalizing more for glucose excursions and less for insulin excursions. For low daily insulin needs, the ratios may be biased towards penalizing more for insulin excursions and less for glucose excursions.

Exemplary embodiments described herein relate to a closed loop artificial pancreas (AP) system. The closed loop AP system seeks to automatically and continuously control the blood glucose (BG) level of a user by emulating the endocrine functionality of a healthy pancreas. The AP system uses a closed loop control system with a cost function. The penalty function helps to bound the infusion rate of insulin to attempt to avoid hypoglycemia and hyperglycemia. However, unlike conventional systems that use a generic or baseline parameter for a user's insulin needs in a cost function, the exemplary embodiments may use a customized parameter in the cost function that reflects the individualized insulin needs of the user. The use of the customized parameter causes the cost function to result in insulin dosages over time better suited to the individualized insulin needs of the user. This helps to smooth the response of user to insulin infusions and helps to better avoid hypoglycemia and hyperglycemia.

In an example, an AP application may be executed by a processor to enable a system to monitor a user's glucose values, determine an appropriate level of insulin for the user based on the monitored glucose values (e.g., BG concentrations or BGmeasurement values) and other information, such as user-provided information, such as carbohydrate intake, meal times or the like, and take actions to maintain a user's BG value within an appropriate range. The appropriate BG value range may be considered a target BG value of the particular user. For example, a target blood BG value may be acceptable if it falls within the range of 80 mg/dL to 120 mg/dL, which is a range satisfying the clinical standard of care for treatment of diabetes. However, an AP application as described herein may account for an activity level of a user to more precisely establish a target BG value and may set the target BG value at, for example, 110 mg/dL, or the like. As described in more detail with reference to the examples herein, the AP application may utilize the monitored BG values and other information to generate and send a command to a wearable drug delivery device including, for example, a pump, to control delivery of insulin to the user, change the amount or timing of future doses, as well as to control other functions.

FIG. 1A illustrates a simplified block diagram of an example of an AP system 100 suitable for practicing an exemplary embodiment. The example AP system 100 may include a controller 102, a pump mechanism or other fluid extraction mechanism 104 (hereinafter "pump 104"), and a sensor 108. The controller 102, pump 104, and sensor 108 may be communicatively coupled to one another via a wired or wireless communication paths. For example, each of the controller 102, the pump 104 and the sensor 108 may be equipped with a wireless radio frequency transceiver operable to communicate via one or more communication protocols, such as Bluetooth®, or the like. The sensor 108 may be a glucose monitor such as, for example, a continuous glucose monitor (CGM) 108. The CGM 108 may, for example, be operable to measure BG values of a user to generate the measured actual BG level signal 112.

As shown in the example, the controller 102 may receive a desired BG level signal 110, which may be a first signal, indicating a desired bloodBG level or range for a user. The desired BG level signal 110 may be received from a user interface to the controller or other device, or by an algorithm that automatically determines a BG level for a user. The sensor 108 may be coupled to the user and be operable to measure an approximate value of an actual BG level of the user. The measured BG value, the actual BG level, the approximate measured value of the actual BG level are only approximate values of a user's BG level, and it should be understood that there may be errors in the measured BG levels. The errors may, for example, be attributable to a number of factors such as age of the sensor 108, location of the sensor 108 on a body of a user, environmental factors (e.g., altitude, humidity, barometric pressure), or the like. The terms measured BG value, actual BG level, approximate measured value of the actual BG level may be used interchangeably throughout the specification and drawings. In response to the measured BG level or value, the sensor 108 generate a signal indicating the measured BG value. As shown in the example, the controller 102 may also receive from the sensor 108 via a communication path, a measured BG level signal 112, which may be a second signal, indicating an approximate measured value of the actual BG level of the user.

Based on the desired BG level signal 110 and the measured actual BG level signal 112, the controller 102 may generate one or more control signals 114 for directing operation of the pump 104. For example, one of the control signals 114 may cause the pump 104 to deliver a dose of insulin 116 to a user via output 106. The dose of insulin 116 may, for example, be determined based on a difference between the desired BG level signal 110 and the actual BG signal level 112. The penalty function referenced above plays a role in determining the dosage as part of the closed loop control system as will be described below. The dose of insulin 116 may be determined as an appropriate amount of insulin to drive the actual BG level of the user to the desired BG level. Based on operation of the pump 104 as determined by the control signals 114, the user may receive the insulin 116 from the pump 104.

In various examples, one or more components of the AP system 100 may be incorporated into a wearable or on body drug delivery system that is attached to the user.

Figure 1B:
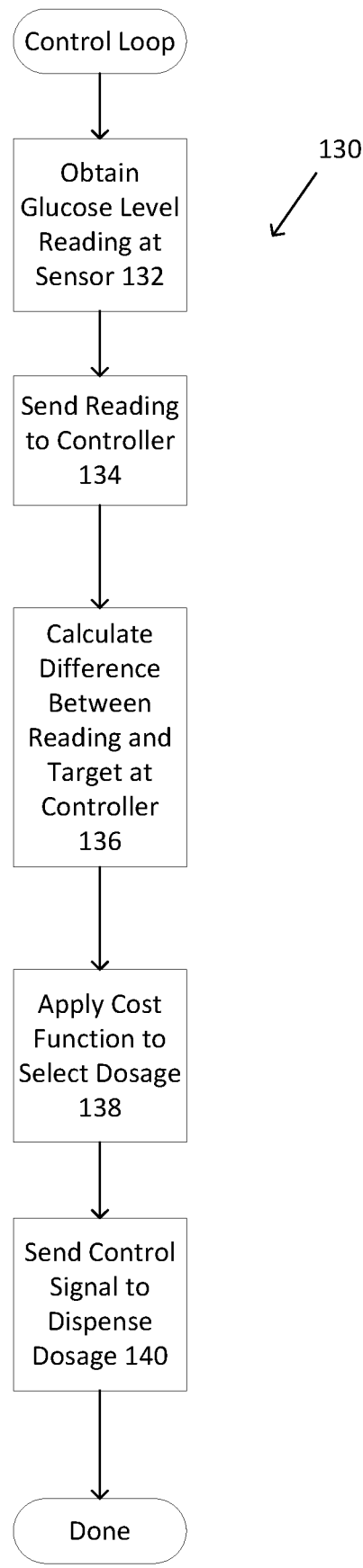
FIG. 1B depicts a flowchart of steps that may be performed by a control loop of the artificial pancreas system.

FIG. 1B depicts a flowchart 130 of steps that may be performed by exemplary embodiments of the AP system in determining what dose of insulin to deliver the user as part of the closed loop control system. Initially, as was described above relative to FIG. 1A, a BG level reading is obtained by the sensor 108 (132). The BG level reading in sent via a signal 112 to the controller 102 (134). The controller 102 calculates an error value as the difference between the measured BG level 112 and the desired BG level 110 (136). The closed loop control system attempts to minimize the aggregate penalty of the cost function over a wide range of possible dosages. The cost function is applied to the possible dosages, and the dosage with the best penalty function value is selected (138). Depending on how the penalty function is configured, the best value may be the lowest value or the highest value. The penalty function used in exemplary embodiments will be described in more below. A control signal 114 may be generated by the controller 102 and sent to the pump 104 to cause the pump to deliver the desired insulin dose to the user (140).

The simplified block diagram of the example AP system 100 provides a general illustration of the operation of the system. An example of a more detailed implementation of devices usable in such an AP system is illustrated in FIG. 2.

Various examples of an AP system include a wearable drug delivery device that may operate in the system to manage treatment of a diabetic user according to a diabetes treatment plan. The diabetes treatment plan may include a number of parameters related to the delivery of insulin that may be determined and modified by a computer application referred to as an AP application.

A wearable drug delivery device as described herein may include a controller operable to direct operation of the wearable drug delivery device via the AP application. For example, a controller of the wearable drug delivery device may provide a selectable activity mode of operation for the user. Operation of the drug delivery device in the activity mode of operation may reduce a probability of hypoglycemia during times of increased insulin sensitivity for the user and may reduce a probability of hyperglycemia during times of increased insulin requirements for the user. The activity mode of operation may be activated by the user or may be activated automatically by the controller. The controller may automatically activate the activity mode of operation based on a detected activity level of the user and/or a detected location of the user.

Figure 2:
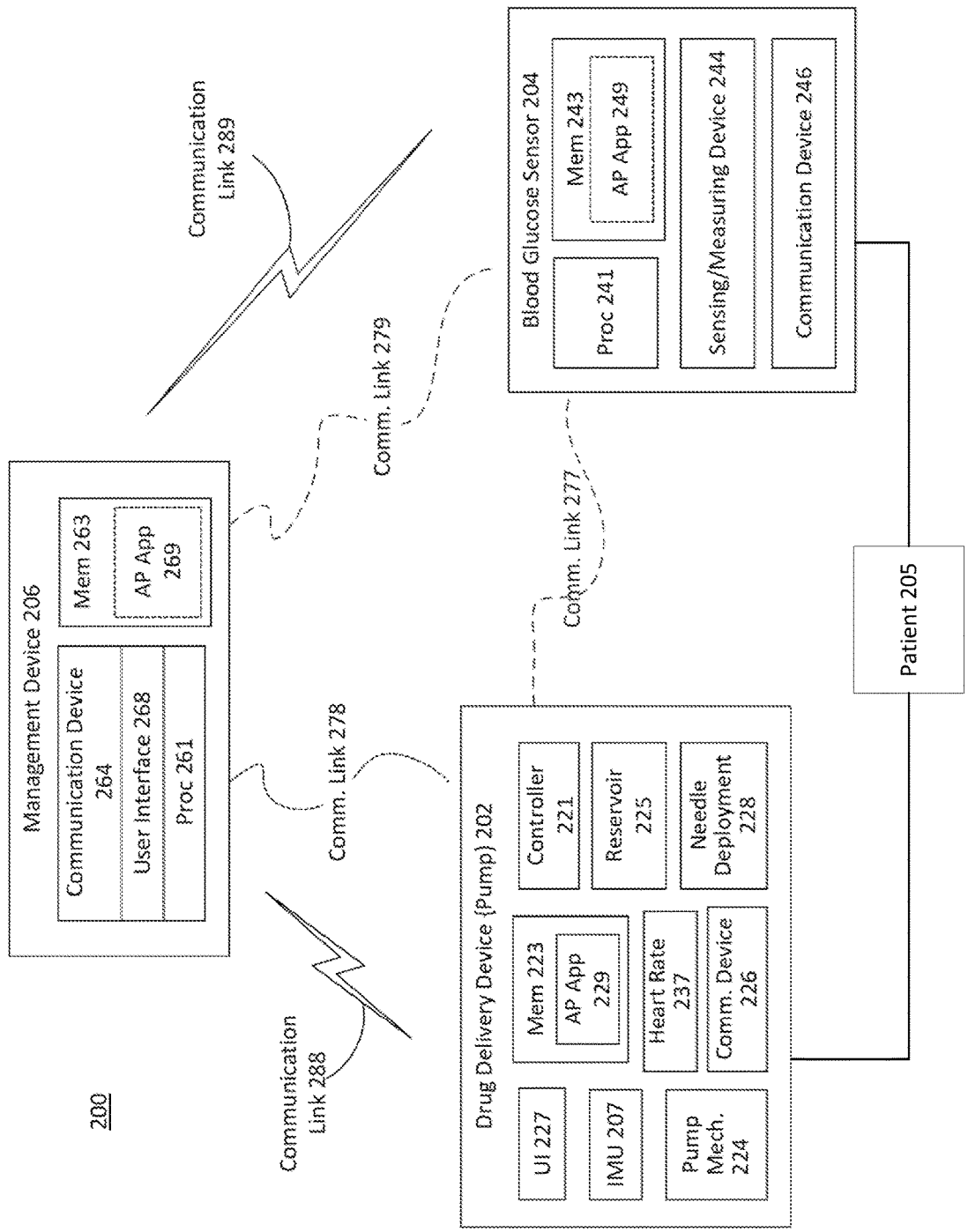
FIG. 2 depicts an illustrative artificial pancreas system in more detail.

FIG. 2 illustrates an example of a drug delivery system. The drug delivery system 200 may include a drug delivery device 202, a management device 206, and a BG sensor 204.

In the example of FIG. 2, the drug delivery device 202 may be a wearable or on-body drug delivery device that is worn by a user on the body of the user. As shown in FIG. 2, the drug delivery device 202 may include an inertial measurement unit (IMU) 207. The drug delivery device 202 may further include a pump mechanism 224 that may, in some examples be referred to as a drug extraction mechanism or component, and a needle deployment mechanism 228. In various examples, the pump mechanism 224 may include a pump or a plunger (not shown).

The needle deployment component 228 may, for example include a needle (not shown), a cannula (not shown), and any other fluid path components for coupling the stored liquid drug in the reservoir 225 to the user. The cannula may form a portion of the fluid path component coupling the user to the reservoir 225. After the needle deployment component 228 has been activated, a fluid path (not shown) to the user is provided, and the pump mechanism 224 may expel the liquid drug from the reservoir 225 to deliver the liquid drug to the user via the fluid path. The fluid path may, for example, include tubing (not shown) coupling the wearable drug delivery device 202 to the user (e.g., tubing coupling the cannula to the reservoir 225).

The wearable drug delivery device 202 may further include a controller 221 and a communications interface device 226. The controller 221 may be implemented in hardware, software, or any combination thereof. The controller 221 may, for example, be a microprocessor, a logic circuit, a field programmable gate array (FPGA), an application specific integrated circuit (ASIC) or a microcontroller coupled to a memory. The controller 221 may maintain a date and time as well as other functions (e.g., calculations or the like) performed by processors. The controller 221 may be operable to execute an AP algorithm stored in the memory that enables the controller 221 to direct operation of the drug delivery device 202. In addition, the controller 221 may be operable to receive data or information indicative of the activity of the user from the IMU 207, as well as from any other sensors (such as those (e.g., accelerometer, location services application or the like) on the management device 206 or CGM 204) of the drug delivery device 202 or any sensor coupled thereto, such as a global positioning system (GPS)-enabled device or the like.

The controller 221 may process the data from the IMU 207 or any other coupled sensor to determine if an alert or other communication is to be issued to the user and/or a caregiver of the user or if an operational mode of the drug delivery device 202 is to be adjusted. The controller 221 may provide the alert, for example, through the communications interface device 226. The communications interface device 226 may provide a communications link to one or more management devices physically separated from the drug delivery device 202 including, for example, a management device 206 of the user and/or a caregiver of the user (e.g., a parent). The communication link provided by the communications interface device 226 may include any wired or wireless communication link operating according to any known communications protocol or standard, such as Bluetooth or a cellular standard.

The example of FIG. 2 further shows the drug delivery device 202 in relation to a BG sensor 204, which may be, for example, a CGM. The CGM 204 may be physically separate from the drug delivery device 202 or may be an integrated component thereof. The CGM 204 may provide the controller 221 with data indicative of measured or detected BG levels of the user.

The management device 206 may be maintained and operated by the user or a caregiver of the user. The management device 206 may control operation of the drug delivery device 202 and/or may be used to review data or other information indicative of an operational status of the drug delivery device 202 or a status of the user. The management device 206 may be used to direct operations of the drug delivery device 202. The management device 206 may include a processor 261 and memory devices 263. The memory devices 262 may store an AP application 269 including programming code that may implement the activity mode, the hyperglycemia protection mode, and/or the hypoglycemia protection mode. The management device 206 may receive alerts, notifications, or other communications from the drug delivery device 202 via one or more known wired or wireless communications standard or protocol.

The drug delivery system 200 may be operable to implement the AP application that includes functionality to determine a movement of a wearable drug delivery device that is indicative of physical activity of the user, implement an activity mode, a hyperglycemia mode, a hypoglycemia mode, and other functions, such as control of the wearable drug delivery device. The drug delivery system 200 may be an automated drug delivery system that may include a wearable drug delivery device (pump) 202, a sensor 204, and a personal diabetes management device (PDM) 206.

In an example, the wearable drug delivery device 202 may be attached to the body of a user 205 and may deliver any therapeutic agent, including any drug or medicine, such as insulin or the like, to a user. The wearable drug delivery device 202 may, for example, be a wearable device worn by the user. For example, the wearable drug delivery device 202 may be directly coupled to a user (e.g., directly attached to a body part and/or skin of the user via an adhesive or the like). In an example, a surface of the wearable drug delivery device 202 may include an adhesive to facilitate attachment to a user.

The wearable drug delivery device 202 may be referred to as a pump, or an insulin pump, in reference to the operation of expelling a drug from the reservoir 225 for delivery of the drug to the user.

In an example, the wearable drug delivery device 202 may include the reservoir 225 for storing the drug (such as insulin), a needle or cannula (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula (not shown), and into the user. The reservoir 225 may be configured to store or hold a liquid or fluid, such as insulin, morphine, or another therapeutic drug. The pump mechanism 224 may be fluidly coupled to reservoir 225, and communicatively coupled to the processor 221. The wearable drug delivery device 202 may also include a power source (not shown), such as a battery, a piezoelectric device, or the like, for supplying electrical power to the pump mechanism 224 and/or other components (such as the processor 221, memory 223, and the communication device 226) of the wearable drug delivery device 202. Although also not shown, an electrical power supply for supplying electrical power may similarly be included in each of the sensor 204, the smart accessory device 207 and the management device (PDM) 206.

In an example, the BG sensor 204 may be a device communicatively coupled to the processor 261 or 221 and may be operable to measure a BGvalue at a predetermined time interval, such as every 5 minutes, or the like. The BG sensor 204 may provide a number of BG measurement values to the AP applications operating on the respective devices. For example, the BG sensor 204 may be a continuous BG sensor that provides BG measurement values to the AP applications operating on the respective devices periodically, such as approximately every 5, 10, 12 minutes, or the like.

The wearable drug delivery device 202 may also include the IMU 207. The IMU 207 may be operable to detect various motion parameters (e.g., acceleration, deceleration, speed, orientation, such as roll, pitch, yaw, compass direction, or the like) that may be indicative of the activity of the user. For example, the IMU 207 may output signals in response to detecting motion of the wearable drug delivery device 202 that is indicative of a status of any physical condition of the user, such as, for example, a motion or position of the user. Based on the detected activity of the user, the drug delivery device 202 may adjust operation related to drug delivery, for example, by implementing an activity mode as discussed herein.

The wearable drug delivery device 202 may when operating in a normal mode of operation may provide insulin stored in reservoir 225 to the user based on information (e.g., blood glucose measurement values, inputs from an inertial measurement unit, global positioning system-enabled devices, Wi-Fi-enabled devices, or the like) provided by the sensor 204 and/or the management device (PDM) 206.

For example, the wearable drug delivery device 202 may contain analog and/or digital circuitry that may be implemented as a controller 221 (or processor) for controlling the delivery of the drug or therapeutic agent. The circuitry used to implement the processor 221 may include discrete, specialized logic and/or components, an application-specific integrated circuit, a microcontroller or processor that executes software instructions, firmware, programming instructions or programming code (enabling, for example, the AP App 229 stored in memory 223, or any combination thereof. For example, the processor 221 may execute a control algorithm, such as an AP application 229, and other programming code that may make the processor 221 operable to cause the pump to deliver doses of the drug or therapeutic agent to a user at predetermined intervals or as needed to bring BG measurement values to a target BG value. The size and/or timing of the doses may be programmed, for example, into an AP application 229 by the user or by a third party (such as a health care provider, wearable drug delivery device manufacturer, or the like) using a wired or wireless link, such as 220, between the wearable drug delivery device 202 and a management device 206 or other device, such as a computing device at a healthcare provider facility. In an example, the pump or wearable drug delivery device 202 is communicatively coupled to the processor 261 of the management device via the wireless link 220 or via a wireless link, such as 291 from smart accessory device 207 or 208 from the sensor 204. The pump mechanism 224 of the wearable drug delivery device may be operable to receive an actuation signal from the processor 261, and in response to receiving the actuation signal and expel insulin from the reservoir 225 and the like.

The devices in the system 200, such as management device 206, smart accessory device 207 and sensor 204, may also be operable to perform various functions including controlling the wearable drug delivery device 202. For example, the management device 206 may include a communication device 264, a processor 261, and a management device memory 263. The management device memory 263 may store an instance of the AP application 269 that includes programming code, that when executed by the processor 261 provides the process examples described herein. The management device memory 263 may also store programming code for providing the process examples described with reference to the examples herein.

Although not shown, the system 200 may include a smart accessory device may be, for example, an Apple Watch®, other wearable smart device, including eyeglasses, provided by other manufacturers, a global positioning system-enabled wearable, a wearable fitness device, smart clothing, or the like. Similar to the management device 206, the smart accessory device (not shown) may also be operable to perform various functions including controlling the wearable drug delivery device 202. For example, the smart accessory device may include a communication device, a processor, and a memory. The memory may store an instance of the AP application that includes programming code for providing the process examples described with reference to the examples described herein. The memory may also as store programming code and be operable to store data related to the AP application.

The sensor 204 of system 200 may be a CGM as described above, that may include a processor 241, a memory 243, a sensing or measuring device 244, and a communication device 246. The memory 243 may store an instance of an AP application 249 as well as other programming code and be operable to store data related to the AP application 249. The AP application 249 may also include programming code for providing the process examples described with reference to the examples described herein.

Instructions for determining the delivery of the drug or therapeutic agent (e.g., as a bolus dosage) to the user (e.g., the size and/or timing of any doses of the drug or therapeutic agent) may originate locally by the wearable drug delivery device 202 or may originate remotely and be provided to the wearable drug delivery device 202. In an example of a local determination of drug or therapeutic agent delivery, programming instructions, such as an instance of the AP application 229, stored in the memory 223 that is coupled to the wearable drug delivery device 202 may be used to make determinations by the wearable drug delivery device 202. In addition, the wearable drug delivery device 202 may be operable to communicate via the communication device 226 and communication link 288 with the wearable drug delivery device 202 and with the BG sensor 204 via the communication device 226 and communication link 289.

Alternatively, the remote instructions may be provided to the wearable drug delivery device 202 over a wired or wireless link by the management device (PDM) 206. The PDM 206 may be equipped with a processor 261 that may execute an instance of the AP application 269, if present in the memory 263. The memory may store computer-readable instructions for execution by the processor 261. The memory may include a non-transitory computer-readable storage media for storing instructions executable by the processor. The wearable drug delivery device 202 may execute any received instructions (originating internally or from the management device 206) for the delivery of insulin to the user. In this way, the delivery of the insulin to a user may be automated.

In various examples, the wearable drug delivery device 202 may communicate via a wireless communication link 288 with the management device 206. The management device 206 may be an electronic device such as, for example, a smart phone, a tablet, a dedicated diabetes therapy management device, or the like. Alternatively, the management device 206 may be a wearable wireless accessory device, such as a smart watch, or the like. The wireless links 287-289 may be any type of wireless link provided by any known wireless standard. As an example, the wireless links 287-289 may enable communications between the wearable drug delivery device 202, the management device 206 and sensor 204 based on, for example, Bluetooth®, Wi-Fi®, a near-field communication standard, a cellular standard, or any other wireless optical or radio-frequency protocol.

The sensor 204 may also be coupled to the user by, for example, adhesive or the like and may provide information or data on one or more medical conditions and/or physical attributes of the user. The information or data provided by the sensor 204 may be used to adjust drug delivery operations of the wearable drug delivery device 202. For example, the sensor 204 may be a glucose sensor operable to measure BG and output a BG value or data that is representative of a BG value. For example, the sensor 204 may be a glucose monitor that provides periodic BG measurements a CGM, or another type of device or sensor that provides BG measurements.

The sensor 204 may include a processor 241, a memory 243, a sensing/measuring device 244, and communication device 246. The communication device 246 of sensor 204 may include an electronic transmitter, receiver, and/or transceiver for communicating with the management device 206 over a wireless link 222 or with wearable drug delivery device 202 over the link 208. The sensing/measuring device 244 may include one or more sensing elements, such as a BG measurement element, a heart rate monitor, a blood oxygen sensor element, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of an AP application 249 that is executable by the processor 241.

Although the sensor 204 is depicted as separate from the wearable drug delivery device 202, in various examples, the sensor 204 and wearable drug delivery device 202 may be incorporated into the same unit. That is, in one or more examples, the sensor 204 may be a part of the wearable drug delivery device 202 and contained within the same housing of the wearable drug delivery device 202 (e.g., the sensor 204 may be positioned within or embedded within the wearable drug delivery device 202). Glucose monitoring data (e.g., measured BG values) determined by the sensor 204 may be provided to the wearable drug delivery device 202, smart accessory device 207 and/or the management device 206, which may use the measured BG values to determine movement of the wearable drug delivery device indicative of physical activity of the user, an activity mode, a hyperglycemia mode and a hyperglycemia mode.

In an example, the management device 206 may be a personal diabetes manager. The management device 206 may be used to program or adjust operation of the wearable drug delivery device 202 and/or the sensor 204. The management device 206 may be any portable electronic device including, for example, a dedicated controller, such as processor 261, a smartphone, or a tablet. In an example, the management device (PDM) 206 may include a processor 261, a management device management device memory 263, and a communication device 264. The management device 206 may contain analog and/or digital circuitry that may be implemented as a processor 261 (or controller) for executing processes to manage a user's BG levels and for controlling the delivery of the drug or therapeutic agent to the user. The processor 261 may also be operable to execute programming code stored in the management device management device memory 263. For example, the management device management device memory 263 may be operable to store AP application 269 that may be executed by the processor 261. The processor 261 may when executing the AP application 269 may be operable to perform various functions, such as those described with respect to the examples. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the wearable drug delivery device 202. The respective transceivers of communication device 264 may be operable to transmit signals containing information useable by or generated by the AP application or the like. The communication devices 226 and 246 of respective wearable drug delivery device 202 and sensor 204, respectively, may also be operable to transmit signals containing information useable by or generated by the AP application or the like.

The wearable drug delivery device 202 may communicate with the sensor 204 over a wireless link 208 and may communicate with the management device 206 over a wireless link 220. The sensor 204 and the management device 206 may communicate over a wireless link 222. The smart accessory device 207, when present, may communicate with the wearable drug delivery device 202, the sensor 204 and the management device 206 over wireless links 287, 288 and 289, respectively. The wireless links 287, 288 and 289 may be any type of wireless link operating using known wireless standards or proprietary standards. As an example, the wireless links 287, 288 and 289 may provide communication links based on Bluetooth®, Wi-Fi, a near-field communication standard, a cellular standard, or any other wireless protocol via the respective communication devices 226, 246 and 264. In some examples, the wearable drug delivery device 202 and/or the management device 206 may include a user interface 227 and 268, respectively, such as a keypad, a touchscreen display, levers, buttons, a microphone, a speaker, a display, or the like, that is operable to allow a user to enter information and allow the management device to output information for presentation to the user.

In various examples, the drug delivery system 200 may be an insulin drug delivery system. For example, the wearable drug delivery device 202 may be the OmniPod® (Insulet Corporation, Billerica, MA) insulin delivery device as described in U.S. Pat. Nos. 7,303,549, 7,137,964, or U.S. Pat. No. 6,740,059, each of which is incorporated herein by reference in its entirety or another type of insulin delivery device.

In the examples, the drug delivery system 200 may implement the AP algorithm (and/or provide AP functionality) to govern or control automated delivery of insulin to a user (e.g., to maintain euglycemia—a normal level of glucose in the blood). The AP application may be implemented by the wearable drug delivery device 202 and/or the sensor 204. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 204). For example, the AP application may determine an appropriate delivery of insulin based on glucose level monitoring of the user through the sensor 204. The AP application may also allow the user to adjust insulin delivery. For example, the AP application may allow a user to select (e.g., via an input) commands for output to the wearable drug delivery device 202, such as a command to set a mode of the wearable drug delivery device, such as an activity mode, a hyperglycemia protect mode, a hypoglycemia protect mode, deliver an insulin bolus, or the like. In one or more examples, different functions of the AP application may be distributed among two or more of the management device 206, the wearable drug delivery device (pump) 202 or the sensor 204. In other examples, the different functions of the AP application may be performed by one device, such the management device 206, the wearable drug delivery device (pump) 202 or the sensor 204. In various examples, the drug delivery system 200 may include features of or may operate according to functionalities of a drug delivery system as described in U.S. patent application Ser. No. 15/359,187, filed Nov. 22, 2016 and Ser. No. 16/570,125, filed Sep. 13, 2019, which are both incorporated herein by reference in their entirety.

As described herein, the drug delivery system 200 or any component thereof, such as the wearable drug delivery device may be considered to provide AP functionality or to implement an AP application. Accordingly, references to the AP application (e.g., functionality, operations, or capabilities thereof) are made for convenience and may refer to and/or include operations and/or functionalities of the drug delivery system 200 or any constituent component thereof (e.g., the wearable drug delivery device 202 and/or the management device 206). The drug delivery system 200—for example, as an insulin delivery system implementing an AP application—may be considered to be a drug delivery system or an AP application-based delivery system that uses sensor inputs (e.g., data collected by the sensor 204).

In an example, the drug delivery device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the wearable drug delivery device (pump) 202 may be transmitted to the cloud-based services 211 for storage or processing via the transceivers of communication device 264. Similarly, wearable drug delivery device 202, management device 206 and sensor 204 may be operable to communicate with the cloud-based services 211 via the communication link 288.

In an example, the respective receiver or transceiver of each respective device 202, 206 or 207 may be operable to receive signals containing respective BG measurement values of the number of BG measurement values that may be transmitted by the sensor 204. The respective processor of each respective device 202, 206 or 207 may be operable to store each of the respective BG measurement values in a respective memory, such as 223, 263 or 273. The respective BG measurement values may be stored as data related to the AP algorithm, such as 229, 249, or 269. In a further example, the AP application operating on any of the management device 206, the smart accessory device 207, or sensor 204 may be operable to transmit, via a transceiver implemented by a respective communication device, 264, 274, 246, a control signal for receipt by a wearable drug delivery device. In the example, the control signal may indicate an amount of insulin to be expelled by the wearable drug delivery device 202.

In an example, one or more of the devices 202, 204, or 206 may be operable to communicate via a wired communication links 277, 278 and 279, respectively. The cloud-based services (not shown) may utilize servers and data storage (not shown). A communication link that couples the drug delivery system 200 to the cloud-based services may be a cellular link, a Wi-Fi link, a Bluetooth link, or a combination thereof, that is established between the respective devices 202, 204, or 206 of system 200. For example, the data storage (not shown) provided by the cloud-based services may store anonymized data, such as user weight, BG measurements, age, meal carbohydrate information, or the like. In addition, the cloud-based services 211 may process the anonymized data from multiple users to provide generalized information related to the various parameters used by the AP application. For example, an age-based general target BG value related to activity levels or particular exercises or sports may be derived from the anonymized data, which may be helpful when a user selects an activity mode (or a hyperglycemia protect mode, or a hypoglycemia protect modes) or the system 200 automatically implements the activity mode (or the hyperglycemia protect, or the hypoglycemia protect modes). The cloud-based services may also provide processing services for the system 200, such as performing a process described with reference to later examples.

The wearable drug delivery device 202 may also include a user interface 227. The user interface 227 may include any mechanism for the user to input data to the drug delivery device 202, such as, for example, a button, a knob, a switch, a touch-screen display, or any other user interaction component. The user interface 227 may include any mechanism for the drug delivery device 202 to relay data to the user and may include, for example, a display, a touch-screen display, or any means for providing a visual, audible, or tactile (e.g., vibrational) output (e.g., as an alert). The user interface 227 may also include additional components not specifically shown in FIG. 2 for sake brevity and explanation. For example, the user interface 227 may include a one or more user input or output components for receiving inputs from or providing outputs to a user or a caregiver (e.g., a parent or nurse), a display that outputs a visible alert, a speaker that outputs an audible, or a vibration device that outputs tactile indicators to alert a user or a caregiver of a potential activity mode, a power supply (e.g., a battery), and the like. Inputs to the user interface 227 may, for example, be a via a fingerprint sensor, a tactile input sensor, a button, a touch screen display, a switch, or the like. In yet another alternative, the activity mode of operation may be requested through a management device 206 that is communicatively coupled to a controller 221 of the wearable drug delivery device 202. In general, a user may generate instructions that may be stored as user preferences in a memory, such as 223 or 263 that specify when the system 200 is to enter the activity mode of operation.

Various operational scenarios and examples of processes performed by the system 200 are described herein. For example, the system 200 may be operable to implement process examples related to an activity mode including a hyperglycemia protect mode and a hypoglycemia protect mode as described in more detail below.

In an example, the drug delivery device 202 may operate as an AP system (e.g., as a portion of the AP system 100) and/or may implement techniques or an algorithm via an AP application that controls and provides functionality related to substantially all aspects of an AP system or at least portions thereof. Accordingly, references herein to an AP system or AP algorithm may refer to techniques or algorithms implemented by an AP application executing on the drug delivery device 202 to provide the features and functionality of an AP system. The drug delivery device 202 may operate in an open-loop or closed-loop manner for providing a user with insulin.

Additional features may be implemented as part of the AP application such as the activity mode, the hyperglycemia mode, the hypoglycemia mode, or the like. For example, the drug delivery device 202 when programming code is executed that enables the activity mode, hyperglycemia mode, hypoglycemia mode or the like of the AP application. As the AP application including the programming code for the activity mode, the hyperglycemia mode, and the hypoglycemia mode is executed, the AP application may adjust operations, such as detecting motion or movement of the wearable drug delivery device that is indicative of physical activity of the user. For example, motion and movement of the wearable drug delivery device 202 that induces motions characteristic of physical activity of the user (e.g., movements, such as jumping, dancing, running, weightlifting, cycling or the like) may be detected by the IMU 207. In addition, the IMU 207, as described with reference to FIG. 3, may include a global positioning system that may detect a location of the wearable drug delivery device 202. Alternatively, or in addition, the wearable drug delivery device 202 may also utilize Wi-Fi location services to determine the location of the wearable drug delivery device 202. For example, the AP algorithm may learn from repeated interaction with the user who may input an indication at particular times that they are about to perform physical activity. Alternatively, or in addition, the wearable drug delivery device 202 may upon detection of a particular location (e.g., gym, sports field, stadium, track, or the like) determine that the user is about to increase their physical activity.

Figure 3:
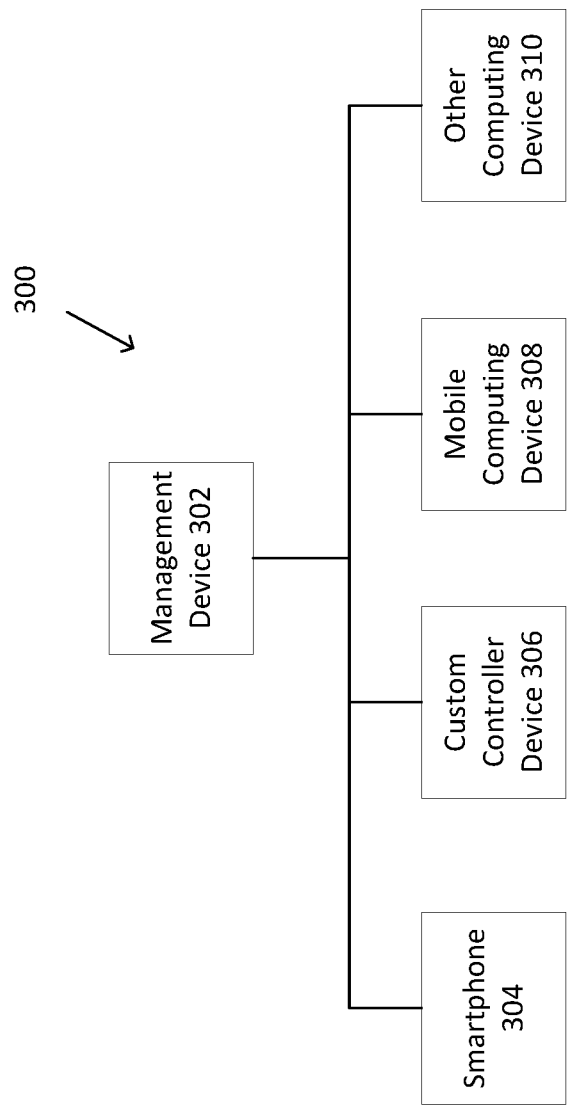
FIG. 3 depicts a diagram of possible types of management devices.

The management device (see e.g., 206 of FIG. 2) may take many different forms. FIG. 3 shows a diagram 300 that illustrates different possible forms for a management device 302. For instance, the management device 302 may be realized in a smartphone 304. Benefits of using the smartphone 304 as the management device 302 include that users typically already own a smartphone 304, and the AP application can be readily installed on a smartphone 304. The management device 302 may also be a custom controller device 306, such as was described above. The management device 302 may also be a mobile computing device 308, such as a tablet computer, a laptop computer, a wearable computing device or the like. Lastly, the management device 302 may be another type of computing device 310, such as a desktop computing device.

In order to appreciate the value of using the customized parameters in the penalty function of the exemplary embodiments, it is helpful to review a generic cost function that may be used in an insulin delivery system. The generic cost function may be expressed as:

$$J(I_{rec}) = Q(f(I_{rec}) - G_{target})^n R(I_{rec} - I_b)^m$$

where J is the total penalty, $I_{rec}$ is the current recommended insulin delivery being assessed for the total penalty, Q is the coefficient of the glucose excursions, $f(I_{rec})$ is any generic function to associate this recommended insulin delivery with a corresponding expected glucose value, $G_{target}$ is the current control target, R is the coefficient for insulin excursions, $I_b$ is the current baseline insulin delivery, and n and m are generic coefficients representing any scaling of the penalties for glucose and/or insulin excursions.

The terms $(f(I_{rec}) - G_{target})$ may be viewed as glucose cost of delivering the recommended dose of insulin. The function $f(I_{rec})$ is a function that associates the recommended insulin delivery dosage with a corresponding expected glucose level of the user. Thus, there is a penalty for the glucose level not being at the target level. The terms ($I_{rec}-I_b$) may be viewed as the insulin cost of delivering the recommended dose of insulin. There is a penalty for the insulin delivery dosage varying from the basal dosage. Q may be viewed as a glucose cost weight coefficient for weighting the glucose cost, and R may be viewed as an insulin cost weight coefficient for weighting the insulin cost. The values of n and m may be set at 2 in many cases.

The coefficients, Q and R, are fixed for all users in a generic case. Thus, if R is fixed at 1000 and a quadratic scaling is used, insulin excursions of 2 U above basal may have a penalty of 4000 for all users. This includes users with varying daily insulin needs. For a user with a total daily insulin (TDI) need of 10 U, the 2 U delivery represents a delivery of 20% of all insulin needed daily. In contrast, the 2 U delivery for a use with a TDI of 100 U represents a delivery of 2% of the daily insulin needs of the user. Hence, the same penalty due to the R coefficient weight may result in an insulin delivery dose that represents greatly different amounts of the TDIs of the respective users.

If the value of Q is fixed to 10, a glucose excursion of 50 mg/dL above the glucose target results in a cost of 25,000 for both users described above. This is the case despite one of the users with a TDI of 10 U requiring 10 times less insulin to cause a drop in glucose of 50 mg/dL than the user with a TDI of 100 U. This example assumes application of the 1800 rule of TDI/1800 (e.g., 10/1800 or 1/180) to determine the ratio of insulin needed to produce a 1 mg/dL drop in glucose. For the user with 10 U TDI, a 50 mg/dL drop requires 50/180 U or 0.28 U. On the other hand, for the user with a 100 U TDI, the ratio is 100/1800 or 1/18 and the amount of insulin needed is 50/18 or 2.8 U. Given this discrepancy, there is a need to scale the coefficients Q and R based on TDI or another metric of daily insulin needs.

As such, the cost function should account for the differing daily insulin needs of the users. The exemplary embodiments attempt to account for such varying needs and may provide the appropriate scaling of the coefficients Q and R.

The exemplary embodiments may modify the coefficients Q and R to account for differing daily insulin needs of users. In one embodiment, the coefficients are calculated as:

$$Q = Q_{base}\left(\frac{P}{P_{base}}\right)^l$$

$$R = R_{base}\left(\frac{P_{base}}{P}\right)^o$$

In these equations, $Q_{base}$ and $R_{base}$ constitute standard baseline coefficients that would be suitable for a user that has generic clinical parameters equivalent to P base. P is the custom value of a user's actual insulin needs.

The values of l and o may be set to have values reflective of a degree of dependence on variation in the user's parameters. In some instances, l or o may have a value of zero so that the associated weight Q or R does not use a scaled cost weight coefficient.

Given the above formulation of the Q and R coefficients, the penalty function for an exemplary embodiment may be expressed as:

$$J(I_{rec}) = Q_{base}\left(\frac{P}{P_{base}}\right)^l (f(I_{rec}) - G_{target})^n + R_{base}\left(\frac{P_{base}}{P}\right)^o (I_{rec} - I_b)^m$$

This formulation of the Q and R coefficients scales the penalization of glucose excursions and insulin excursions. A glucose excursion is an instance where the BG level varies from a target BG level, and an insulin excursion is an instance where the insulin dosage varies from the basal insulin dosage. The cost on glucose excursions increases with higher parameters $$\left(e.g., \left(\frac{P}{P_{base}}\right)\right),$$

whereas the cost on insulin excursions increases with lower parameters $$\left(e.g., \left(\frac{P_{base}}{P}\right)\right).$$

Hence, for a user with large insulin needs, the cost is high, which implies that a larger amount of insulin is needed to return a high glucose excursion to target. Likewise, for a user with small insulin needs, the cost on insulin excursions is high, which implies that any insulin delivery is a larger portion of the user's daily insulin needs.

Figure 4:
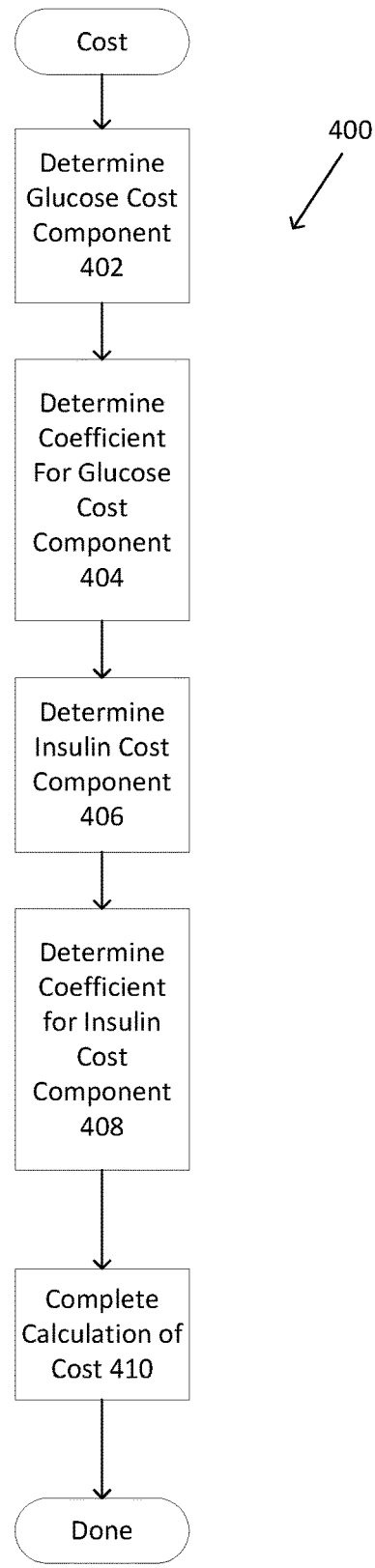
FIG. 4 depicts a flowchart of illustrative steps for calculating a cost with a cost function.

FIG. 4 depicts a flowchart 400 that summarizes the illustrative steps that may be taken for calculating the cost per the penalty function for a proposed insulin dose. The controller may determine the glucose cost component, such as $(f (I_{rec})-G_{target})^n$ (402). The controller calculates the glucose cost weight coefficient, such as $$Q_{base}\left(\frac{P}{P_{base}}\right)^l. \tag{404}$$

The controller may also calculate the insulin cost component, such as $(I_{rec}-G_{target})^n$ (406). The controller may calculate the insulin cost weight coefficient, such as $$R_{base}\left(\frac{P_{base}}{P}\right)^o. \tag{408}$$

Lastly, the controller may complete the calculation of the cost for the dose of insulin per the above equation for the penalty function (410). This cost is determined for each proposed dose of insulin to identify the dosage with the best cost (e.g., the lowest cost dosage).

Figure 5:
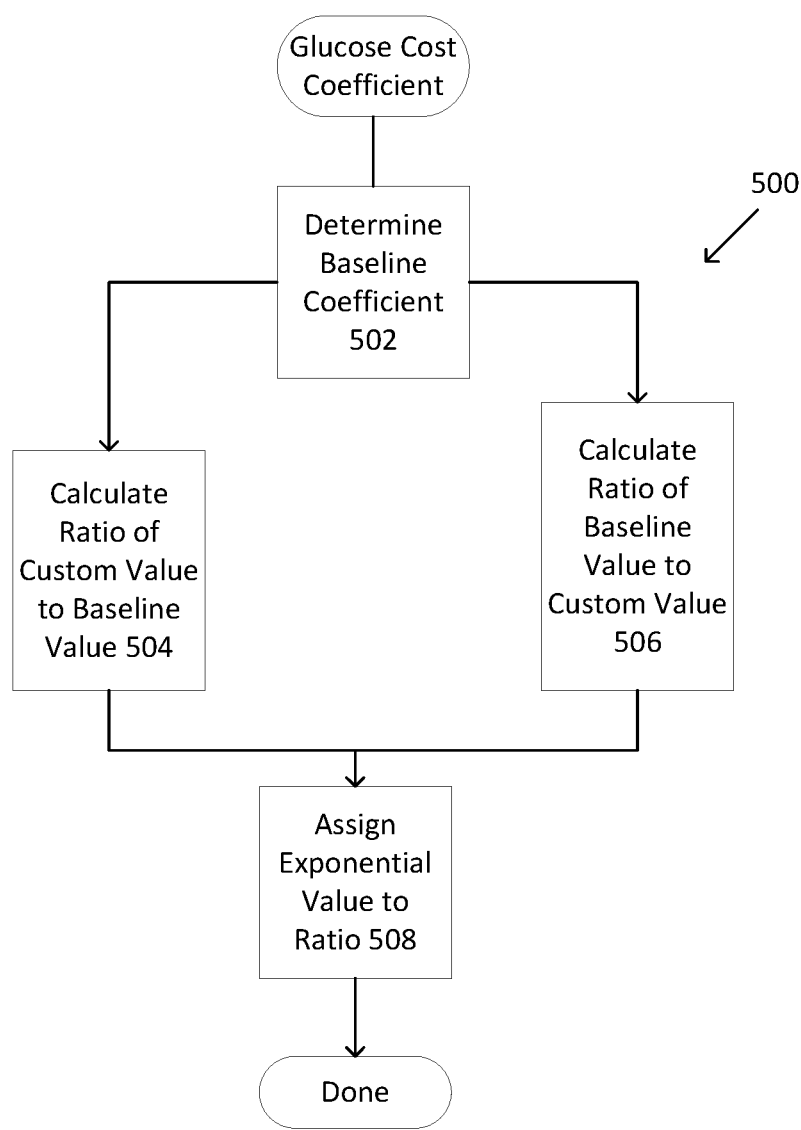
FIG. 5 depicts a flowchart of illustrative steps that may be performed to determine a glucose cost weight coefficient.

In determining the glucose cost weight coefficient, different formulations may be used for different exemplary embodiments. FIG. 5 provides a flowchart 500 of illustrative steps that may be performed to determine the glucose cost weight coefficient. Initially, the baseline value for the parameter (e.g., P) is determined (502). Where TDI is used, the value may be 120 U. Then, there are two options for calculating the ratio used to scale $Q_{base}$. In the example case described above, the ratio is of custom value to the baseline value is calculated $$\left(e.g., \left(\frac{P}{P_{base}}\right)\right). \tag{504}$$

Conversely, a reciprocal ratio instead may be calculated. The reciprocal value is the ratio of the baseline to the custom value $$\frac{P_{base}}{P}. \quad (506)$$

Then, an exponential value (e.g., 1) may be applied to the ratio (506).

Figure 6:
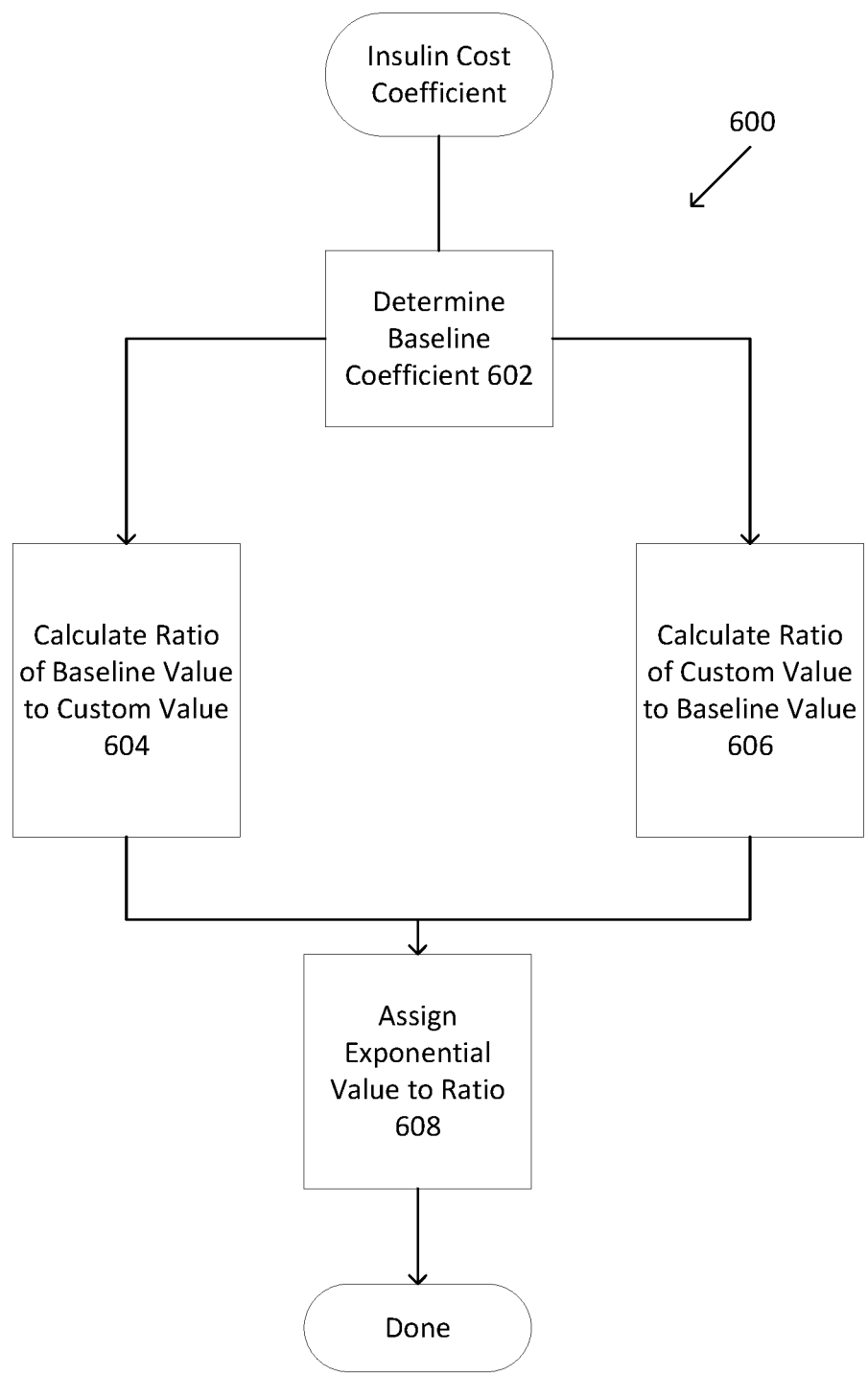
FIG. 6 depicts a flowchart of illustrative steps that may be performed to determine an insulin cost weight coefficient.

Similarly, as shown in the flowchart 600 of FIG. 6, the insulin cost weight coefficient Q may be determined in different manners. Initially, the baseline insulin cost weight coefficient (e.g. $Q_{base}$) is determined (602). The ratio used to scale the baseline insulin cost weigh coefficient may be determined as the ratio of baseline parameter of daily insulin needs to custom daily insulin needs of the user $$\left(e.g., \frac{P_{base}}{P}\right). \quad (604)$$

Alternatively, the inverse ratio may be used $$\left(e.g., \frac{P}{P_{base}}\right). \quad (606)$$

The exponents for the ratios may be assigned as discussed above (608).

Figure 7:
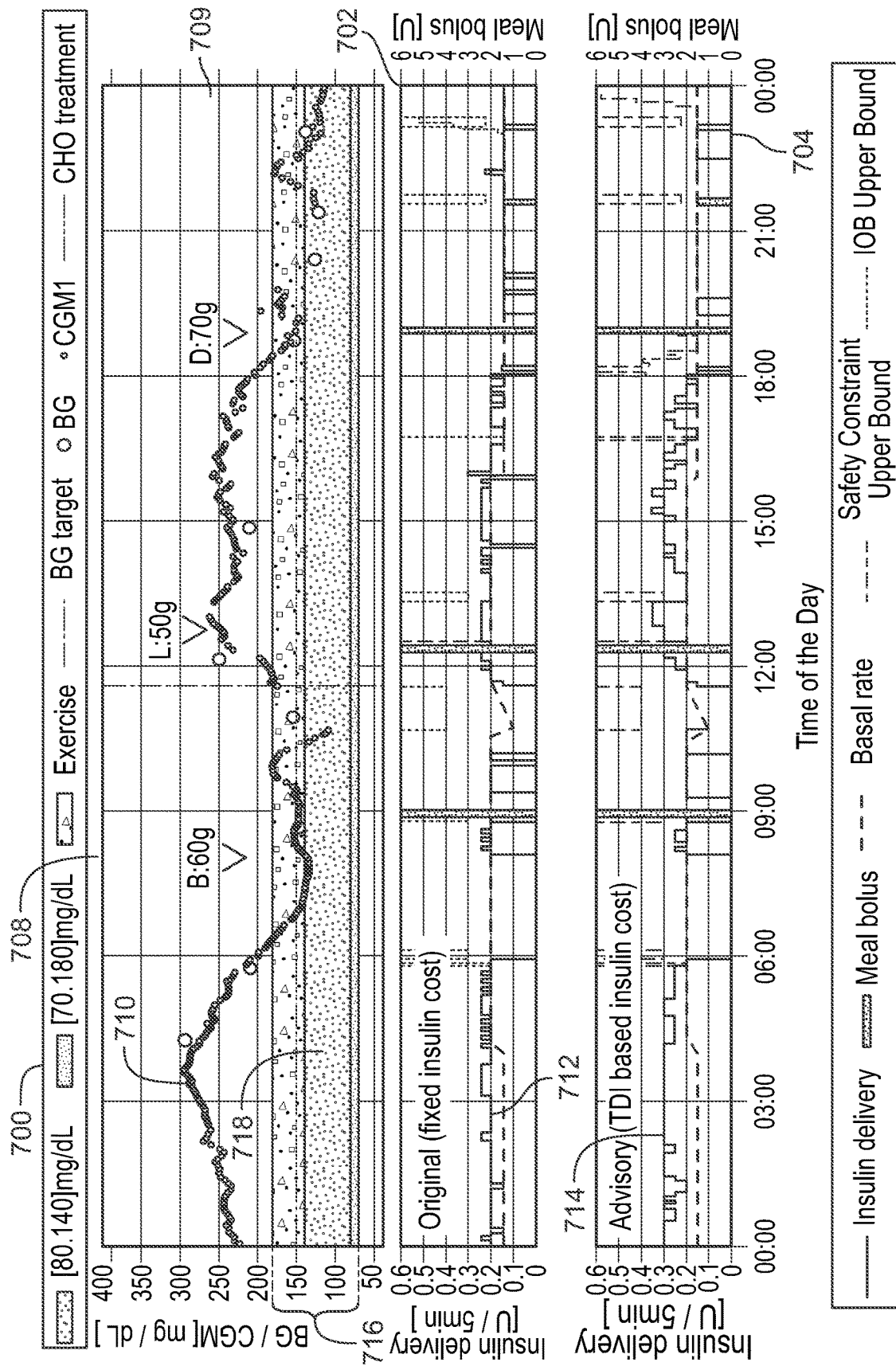
FIG. 7 depicts illustrative plots of a curve of blood glucose levels and curves of insulin delivery for an example with a user having a very high total daily insulin.

The effect of the scaling of the cost weight coefficients can be seen in the plots 700, 702 and 704 of FIG. 7. These plots 700, 702 and 704 are for a user with a very high TDI of 115 U. Plot 700 shows the BG level of a user over time in a worst case scenario using non-scaled cost weight coefficients, and plot 702 shows the insulin delivery over time for such a case. The first portion 708 of the plot 700 shows that the curve 710 of BG levels stays above 250 mg/dL for a long period beginning at around midnight and extending to around 5:00 am since the insulin deliveries did not increase above 0.2 U for an extended time until around 3:00 am as indicated by curve 712 in plot 702. This is the product of the high weight for insulin excursions.

In contrast, with the scaled cost weight coefficients, the doses of insulin increase sooner (e.g., 0.3 U starting 12:00 am) and stay elevated longer at a sooner time as indicated by curve 714 in plot 704. This causes the elevated glucose level to be reduced more quickly. As mentioned above, for users that are insulin resistant, the scaling may allow larger doses of insulin to be delivered.

The insulin excursion penalty is reduced and the glucose excursion penalty is increased by the scaling. Moreover, the curve 710 enters a range of hypoglycemic risk as indicated by the regions 716 and 718 with the non-scaled cost-weight coefficients for the overnight period between 9:00 pm till 12:00 pm in the second part 709 of the plot 702. This is because of the relatively high insulin penalty relative to the user's input basal of roughly 2U per hour. Thus, it is difficult to vary dose much from the basal without incurring a large penalty.

In contrast, with the scaled cost weight coefficients, the insulin excursion penalty is not so great so the insulin amounts may vary more and avoid the extended period of hypoglycemic risk (see that the dose drops on curve 714 to 0 U beginning at around 7:30 pm until 9:00 pm).

Figure 8:
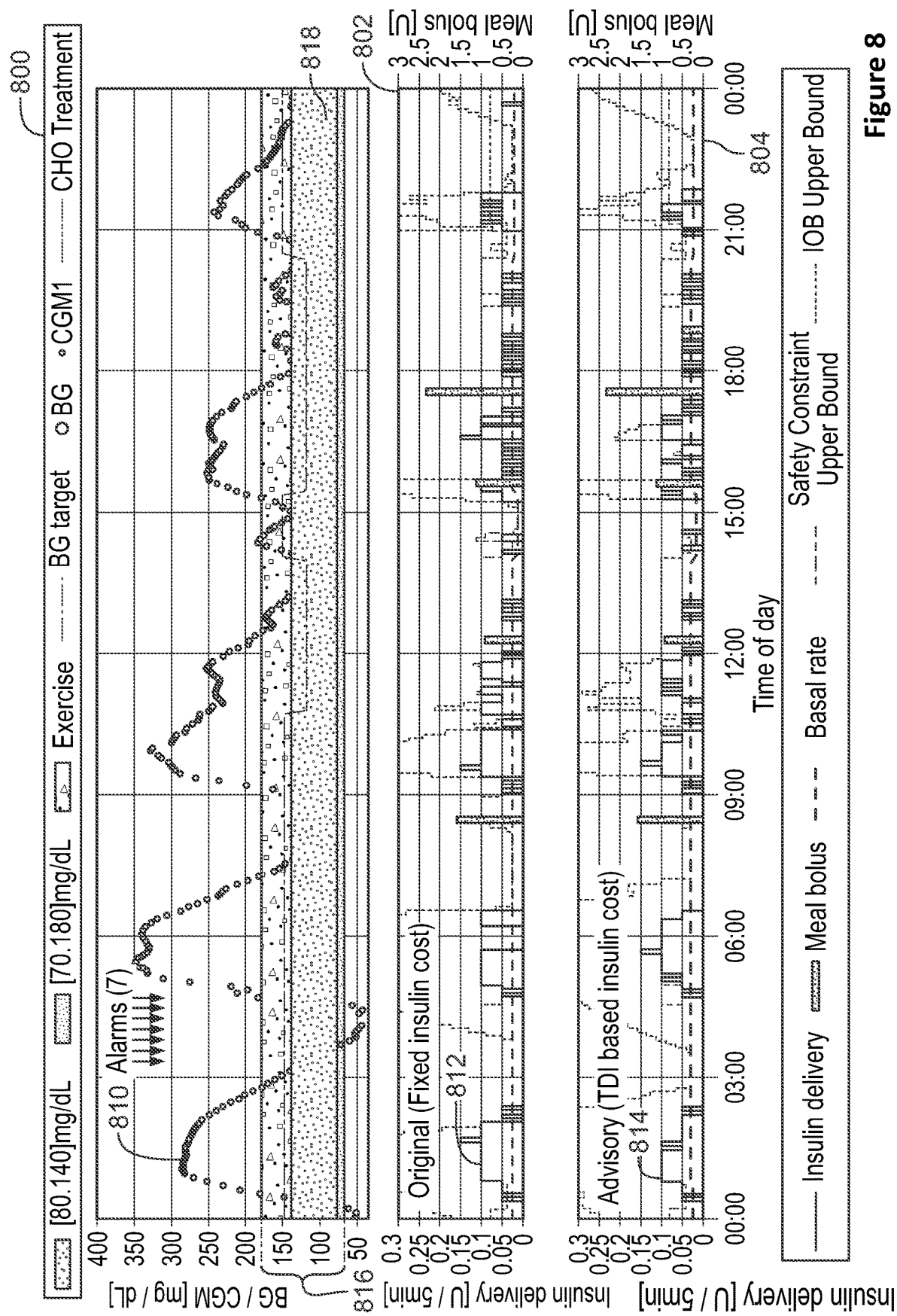
FIG. 8 depicts illustrative plots of a curve of blood glucose levels and curves of insulin delivery for an example with a user having a low total daily insulin.

FIG. 8 shows similar plots 800, 802 and 804 for an example with a user that has a very low TDI of 15 U. Plot 800 shows a user's BG level over time as indicated by curve 810 at 5 minute intervals. Regions 816 and 818 are shaded. As shown, the user's glucose level increased rapidly between 12:00 am and 1:00 am to exceed 200 mg/dL and hover close to 300 mg/dL. Thus, the patient was hyperglycemic during this interval. The system without scaling of the cost weigh coefficients continues to recommend delivery dosages close to the 4 times constraint (e.g., 4×basal) for over an hour as indicated by curve 812 in plot 802. The BG level of the user plummets in response resulting hypoglycemia between 4:00 am and 5:00 am because too much insulin was delivered without violating the constraint. The glucose level spikes and overshoots target when the insulin delivery is halted in response to the hypoglycemia.

In contrast, with the scaled cost weight coefficients, the amount of insulin delivered is reduced and reduced sooner as shown by curve 814 in plot 804 when the user's glucose level begins to fall. This is because the penalty on insulin excursions is higher for such a user whereas the penalty on glucose excursions is lower. Thus, avoiding the overshoot and the resulting hypoglycemia. This may also avoid the hyperglycemia that results from halting the insulin in response to the hypoglycemia.

Figure 9:
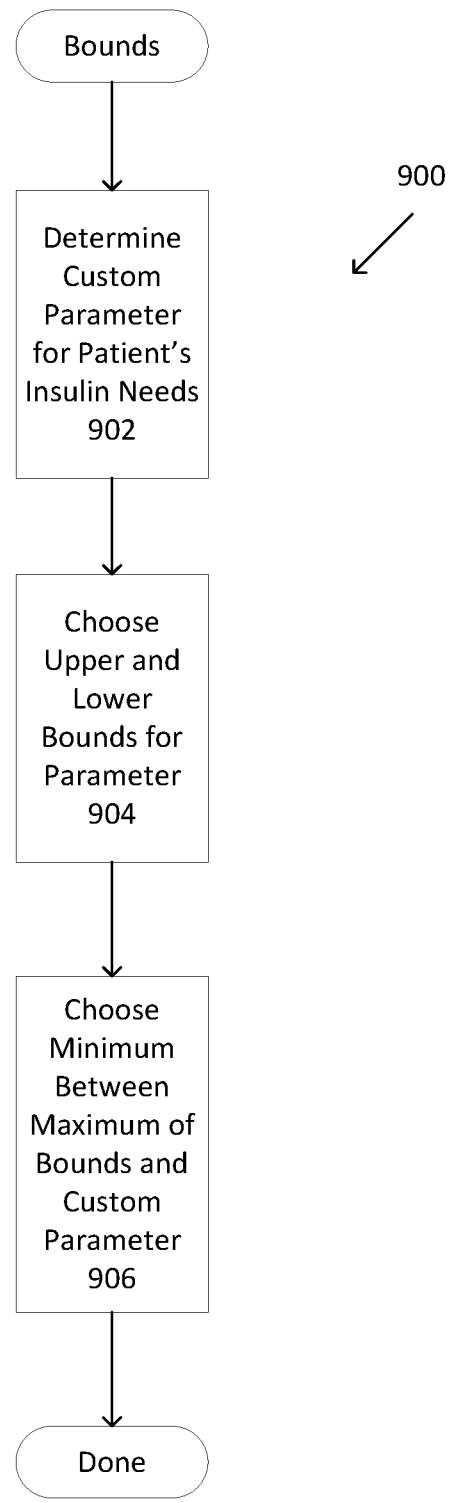
FIG. 9 depicts a flowchart of illustrative steps that may be performed in using bounds on a parameter used in a penalty function.

The value of the cost weight coefficients may be bounded to not exceed low bounds and/or high bounds. FIG. 9 shows a flowchart 900 of steps that may be performed to use such bounds. In one example case, the value of the parameter P is calculated as follows:

$$P = \min(\max(P_{actual}, P_{low}), P_{high})$$

This results in the cost function being:

$$J(I_{rec}) = Q_{base}\left(\frac{\min(\max(P_{actual}, P_{low}), P_{high})}{P_{base}}\right)^l (f(I_{rec}) - G_{target})^n$$
$$+ R_{base}\left(\frac{P_{base}}{\min(\max(P_{actual}, P_{low}), P_{high})}\right)^o (I_{rec} - I_b)^m$$

Hence, to realize these bounds, the custom parameter for the user's insulin needs $P_{actual}$ is calculated (902). The upper bounds $P_{high}$ and the lower bounds $P_{low}$ are determined (904). The minimum among the bounds $P_{high}$ and $P_{low}$ is determined and compared with $P_{actual}$ to identify a largest value (e.g., a maximum), which is used as the value P in the ratios of the cost weight coefficients (906). The use of the bounds may help to keep the ratios from getting too large or too small.

The cost function may be modified to account for user specific values other than TDI. For instance, the cost function may include other clinical parameters, such as basal, correction factor or insulin to carbohydrate ratio. The scaling need not depend on a single parameter like TDI but can instead depend on a combination of multiple parameters. Specifically, the variables represented by P in the earlier representations generally define the user's actual insulin needs. However, although the user's insulin needs can generally be defined by the TDI, their needs can also be defined by their basal parameters, correction factor parameters, or insulin to carbohydrate ratio parameters.

For instance, the generic baseline clinical parameter $P_{base}$ can be defined as the average TDI of the overall population for a typical person with Type 1 Diabetes. On the other hand, this parameter can also be defined as the average basal parameter of a typical person with Type 1 Diabetes.

In alternate embodiments, $P_{base}$ can also be defined as varying combinations of average values of the TDI and basal parameters, such as the following equation:

$$P_{base} = TDI_{avg}^{W_{TDI}} * basal_{avg}^{W_{basal}}$$

Where $W_{TDI}$ and $W_{basal}$ represent the weighting of the TDI and basal parameters to calculate the dependency of the cost function on each parameter. It is important to note that both the TDI and basal parameters have a direct relationship with the user's insulin needs i.e. the higher the user's insulin needs, the higher the value, leading to this form of the equation.

Accordingly, $P_{actual}$ can be defined similarly as: $P_{actual} = TDI_{actual}^{W_{TDI}} * basal_{actual}^{W_{basal}}$ In further embodiments, the Correction factor may be utilized in similar manner as TDI and basal in the above equations. However, the Correction Factor and similar parameters increase in value with decreased insulin needs, and vice versa; therefore, $P_{base}$ and $P_{actual}$ can be calculated as in the following equations:

$$P_{base} = \frac{1}{CF_{avg}^{W_{CF}}}$$

$$P_{actual} = \frac{1}{CF_{actual}^{W_{CF}}}$$

The combination of all three parameters, or other parameters, can also be utilized to calculate $P_{base}$ and $P_{actual}$ as in above. In one embodiment, these calculations can be formulated as in the following equations:

$$P_{base} = \frac{TDI_{avg}^{W_{TDI}} * basal_{avg}^{W_{basal}}}{CF_{avg}^{W_{CF}}}$$

$$P_{actual} = \frac{TDI_{actual}^{W_{TDI}} * basal_{actual}^{W_{basal}}}{CF_{actual}^{W_{CF}}}$$

Other parameters that have a direct relationship (i.e. increase in insulin needs results in increase in value of clinical parameters) can be added to the denominator of the equations for $P_{base}$ and $P_{actual}$, and parameters that have an inverse relationship (i.e. increase in insulin needs results in decrease in value of clinical parameters) can be added to the denominator of the equations for $P_{base}$ and $P_{actual}$.

While the present invention has been described herein with reference to exemplary embodiments, it should be appreciated that various changes in form and detail may be made without departing form the intended scope of the present invention as defined in the appended claims.

The invention claimed is:

1. An insulin delivery device for delivering insulin to a user, comprising:
a non-transitory computer-readable storage medium for storing computer programming instructions;
a processor configured to execute the computer programming instructions to implement a control loop to control the delivery of insulin by the insulin delivery device, wherein the processor selects an insulin delivery dose for a next delivery among delivery dose options that has a best cost function value and wherein the cost function:
has a glucose cost component reflective of a difference between a glucose level that the dose option is predicted to produce for the user and a target glucose level for the user,
has a glucose cost weight coefficient for weighting the glucose cost component, and
wherein the glucose cost weight coefficient has a value customized for the user.

2. The insulin delivery device of claim 1, wherein the processor is additionally configured to execute the computer programming instructions to deliver the selected insulin delivery dose.

3. The insulin delivery device of claim 1, wherein the glucose cost weight coefficient has a value of a baseline glucose cost weight coefficient multiplied by a value indicative of a ratio of a custom value representative of insulin needs of the user to a baseline value representative of insulin needs.

4. The insulin delivery device of claim 1, wherein the cost function has an insulin cost component reflective of how the dose option differs from a current baseline insulin dose.

5. The insulin delivery device of claim 4, wherein the insulin cost component has an insulin cost weight coefficient for weighting the insulin cost component that is customized to the user.

6. The insulin device of claim 5, wherein the insulin cost weight coefficient has a value of a baseline insulin cost weight coefficient multiplied by a value indicative of a ratio of a baseline value representative of insulin needs to a custom value representative of insulin needs of the user.

7. The insulin delivery device of claim 5, wherein the processor enforces bounds on a parameter used in determining at least one of the glucose cost weight coefficient or the insulin cost weight coefficient that is customized for the user.

8. The insulin delivery device of claim 5, wherein the processor is configured to determine at least one of the glucose cost weight coefficient or the insulin cost weight coefficient based on at least one of a correction factor for insulin sensitivity for the user, an insulin to carbohydrate ratio for the user or a basal insulin level for the user.

9. The insulin delivery device of claim 5, wherein at least one of the glucose cost weight coefficient and the insulin cost weight coefficient have values customized for the Total Daily Insulin (TDI) user.

10. A method performed by a processor of an insulin delivery device, comprising:
receiving a glucose reading for a user from a glucose monitor at the processor;
determining with the processor a dose for a next delivery of insulin to the user from the insulin delivery device, wherein the determining comprises:
applying a cost function to a plurality of possible doses of insulin to the user, and
selecting one of the possible doses of insulin that has a best cost under the cost function;
wherein the cost function:
has a glucose cost component reflective of a difference between a glucose level that the dose option is predicted to produce for the user and a target glucose level for the user,
has a glucose cost weight coefficient for weighting the glucose cost component, and
wherein the glucose cost weight coefficient has a value customized for the user; and
with the processor, directing the insulin delivery device to deliver the selected dose of insulin to the user.

11. The method of claim 10, wherein the cost function has an insulin cost component reflective of a difference between an insulin amount of the dose option and a current baseline insulin dose.

12. The method of claim 11, wherein the cost function has an insulin cost weight coefficient for weighing the insulin cost component and the insulin cost weight coefficient is customized for the user.

13. The method of claim 10, wherein the glucose cost weight coefficient has a value of a baseline glucose cost weight coefficient multiplied by a value indicative of a ratio of a custom value representative of insulin needs of the user to a baseline value representative of insulin needs.

14. A non-transitory computer-readable storage device storing computer-readable instructions that cause a processor of an insulin delivery device to perform the following:
receive a glucose reading for a user from a glucose monitor;
determine a dose for a next delivery of insulin to the user from the insulin delivery device, wherein the determining comprises:
applying a cost function to a plurality of possible doses of insulin to the user, and
selecting one of the possible doses of insulin that has a best cost under the cost function;
wherein the cost function:
has a glucose cost component reflective of a difference between a glucose level that a dose option is predicted to produce for the user and a target glucose level for the user,
has a glucose cost weight coefficient for weighting the glucose cost component;
wherein the glucose cost weight coefficient has a value customized for the user; and
direct the insulin delivery device to deliver the selected dose to the user.

15. The non-transitory computer-readable storage medium of claim 14, wherein the glucose cost weight coefficient has a value of a baseline glucose cost weight coefficient multiplied by a value indicative of a ratio of a custom value representative of insulin needs of the user to a baseline value representative of insulin needs.

16. The non-transitory computer-readable storage medium of claim 15, wherein the cost function has an insulin cost component reflective of how the dose option differs from a current baseline insulin dose.

17. The non-transitory computer-readable storage medium of claim 16, wherein the insulin cost weight coefficient has a value of a baseline insulin cost weight coefficient multiplied by a value indicative of a ratio of a baseline value representative of insulin needs to a custom value representative of insulin needs of the user.

18. The non-transitory computer-readable storage medium of claim 16, wherein the determining of at least one of the glucose cost weight coefficient or the insulin cost weight coefficient is based on at least one of a correction factor for insulin sensitivity for the user, an insulin to carbohydrate ratio for the user or a basal insulin level for the user.

19. The non-transitory computer-readable storage medium of claim 18, wherein at least one of the glucose cost weight coefficient and the insulin cost weight coefficient have values customized for the Total Daily Insulin (TDI) user.

20. The non-transitory computer-readable storage medium of claim 16, wherein the processor enforces bounds on a parameter used in determining at least one of the glucose cost weight coefficient or the insulin cost weight coefficient that is customized for the user.

* * * * *